United States Patent
Demharter et al.

(10) Patent No.: US 8,521,258 B2
(45) Date of Patent: *Aug. 27, 2013

(54) CORRECTION METHOD AND MAGNETIC RESONANCE DEVICE

(75) Inventors: Nikolaus Demharter, Dormitz (DE); Michael Frank, Erlangen (DE); Sven Heggen, Erlangen (DE); Ernst Mustafa, Fürth (DE); Jürgen Rößler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 285 days.

This patent is subject to a terminal disclaimer.

(21) Appl. No.: 12/386,327

(22) Filed: Apr. 16, 2009

(65) Prior Publication Data

US 2009/0270715 A1 Oct. 29, 2009

(30) Foreign Application Priority Data

Apr. 25, 2008 (DE) .......... 10 2008 020 780

(51) Int. Cl.
*A61B 5/00* (2006.01)
(52) U.S. Cl.
USPC .......... 600/411; 600/413; 600/424; 600/509; 600/407
(58) Field of Classification Search
USPC .......... 600/411, 413, 509
See application file for complete search history.

(56) References Cited

U.S. PATENT DOCUMENTS

| | | | | |
|---|---|---|---|---|
| 7,221,973 | B2 * | 5/2007 | Nitz | 600/411 |
| 2007/0007960 | A1 | 1/2007 | King | |

OTHER PUBLICATIONS

Jacques Felblinger, Johannes Slotboom et al; Restoration of Electrophysical Signals Distorted by Inductive Effects of Magnetic Field Gradients During MR Sequences; Magnetic Resonance in Medicine 41:715-721; Magazine; 1999.
Freddy Odille, Cédric Pasquier et al; Noise Cancellation Signal Processing Method and Computer System for Improved Real-Time Electrocardiogram Artifact Correction During MRI Data Acquisition; IEEE Transactions on Biomedical Engineering, vol. 54, No. 4, Apr. 2007; Magazine; 2007.

* cited by examiner

*Primary Examiner* — Unsu Jung
*Assistant Examiner* — Phong K Huynh

(57) ABSTRACT

The invention relates to a correction method for correcting interference due to gradient injections in ECG signal data records recorded in a magnetic resonance device by an ECG measuring device. A first correction data record is determined with the ECG measuring device located in a first position. A second correction data record is determined by the ECG measuring device located in a second position. An ECG signal data record is measured by the ECG measuring device located in a defined position. A modified correction data record is defined as a function of the first correction data record and the second correction data record and the first and second position and the defined position of the ECG measuring device. The ECG signal data record is corrected based on the modified correction data record.

13 Claims, 2 Drawing Sheets

CORRECTION METHOD AND MAGNETIC RESONANCE DEVICE

CROSS REFERENCE TO RELATED APPLICATIONS

This application claims priority of German application No. 10 2008 020 780.2 filed Apr. 25, 2008, which is incorporated by reference herein in its entirety.

FIELD OF THE INVENTION

The invention relates to a correction method for correcting interference due to gradient injections in ECG signal data records and a magnetic resonance device, with which the correction method can be implemented.

BACKGROUND OF THE INVENTION

ECG measuring devices are primarily used to measure and monitor the cardiac function of a patient, for which purpose the total voltage of the electrical activity of the myocardial fibers is typically measured as what is known as an "ECG signal" by way of at least two electrodes.

There are however further applications. For example ECG signals are also used in medical imaging to generate trigger signals. During imaging the ECG signal is used to obtain information about the cardiac phase, in order thus to synchronize imaging with cardiac activity. In particular with imaging methods which require a fairly long recording time it is thus possible to produce high-quality cardiac recordings as well as recordings of regions moved by the heartbeat.

ECG measuring devices for the in-situ recording of ECG signals are also used while a patient is being examined using a magnetic resonance device. However operation in the magnetic resonance device, because of the strong gradient fields and high-frequency fields used therein for imaging purposes, means that the ECG measuring device has to meet particular requirements in order to prevent mutual interference between the magnetic resonance device and the ECG measuring device. ECG measuring devices, which are magnetic resonance-compatible in the above sense, are available on the market.

As always a major problem for reliable ECG signal measurement is magnetic fields, which change over time, as used in the magnetic resonance device as magnetic gradient fields for local coding. According to the law of induction such magnetic fields, which change over time, generate interference voltages, which are injected as interference in the ECG signal recorded by the ECG electrodes. Such magnetically generated interference signals are superimposed on the ECG signal generated by the heart and falsify it.

A signal data record $U1(t)$ measured at a first channel of the ECG measuring device then contains not only the desired ECG signal U1 ECG(t) at time t, but a superposition of the ECG signal and the interference voltages $S1(t)$ generated by induction at time t:

$$U1(t)=U1\ ECG(t)+S1(t).$$

This interference is extremely undesirable. Synchronization of a recording of a magnetic resonance image with the heartbeat requires reliable identification of the R-wave of the ECG signal. The interference signals can be interpreted erroneously as an R-wave, for example because of their often similar form, and can therefore wrongly initiate the triggering of a recording of a magnetic resonance image. On the other hand it can also happen that a "true" R-wave is not identified as such because of the superimposed interference signals. This regularly causes a significant deterioration in image quality.

Known from the publications "Restoration of Electrophysiological Signals Distorted by Inductive Effects of Magnetic Field Gradients During MR Sequences"; Jacques Felblinger, Johannes Slotboom, Roland Kreis, Bruno Jung, Chris Boesch; Magnetic Resonance in Medicine 41:715-721 (1999), and "Noise Cancellation Signal Processing Method and Computer System for Improved Real-Time Electrocardiogram Artifact Correction during MRI Data Acquisition"; Freddy Odille, Cedric Pasquier, Roger Abächerli, Pierre-Andre Vuissoz, Gary P. Zientara, Jacques Felblinger; IEEE Transactions on Biomedical Engineering, VOL. 54, NO. 4, APRIL 2007, is a method, in which the interference injections caused by the gradient fields and therefore the interference voltages are estimated. The estimated interference voltage of an ECG channel $S1(t)$ is then subtracted from the ECG signals $U1(t)$ measured at the same ECG channel, to obtain a corrected ECG signal U1 corr(t):

$$U1\ corr(t)=U1\ ECG(t)+S1(t)-S1\ est(t).$$

It is assumed here that the interference voltages $S1(t)$ can be separated into interference voltages $S1x(t)$, $S1y(t)$ and $S1z(t)$, caused respectively by the known currents Ix(t), Iy(t) and Iz(t) applied to the x, y and z axis gradient coils:

$$S1(t) = S1x(t) + S1y(t) + S1z(t)$$
$$= hIxU1(t)*Ix(t) + hIyU1(t)*Iy(t) + hIzU1(t)*Iz(t).$$

Here h Ii $U1(t)$ (i=x,y,z) is the respective pulse response, which characterizes the influence of the current Ii(t) through the i-axis gradient coil on the ECG signal $U1(t)$. "*" characterizes a systems theory convolution. The axes x, y and z are perpendicular to one another here, with the x-axis typically corresponding to a normal vector to a sagittal plane, the y-axis a normal vector to a coronary plane and the z-axis a normal Vector to a transverse plane through a patient in a magnetic resonance device.

The above-mentioned pulse responses h Ii $U1(t)$ are estimated in that ECG signals $U1(t)$ are measured in training measurements for example, when a current Ii(t) not equal to zero is applied respectively to just one of the gradient coils, so that the following applies for i=x for example:

$$U1(t)=U1\ ECG(t)+h\ Ix\ U1(t)*Ix(t).$$

It is possible to estimate the pulse response h Ix $U1(t)$ from this equation means of calculations in the frequency range. In this process the contribution of U1 ECG(t) can be calculated out for example by multiple measurement of $U1(t)$ and subsequent averaging. The procedure is similar for the further pulse responses. The following thus results:

$$S1\ est(t)=h\ Ix\ U1\ est(t)*Ix(t)+h\ Iy\ U1\ est(t)*Iy(t)+h\ Iz\ U1\ est(t)*Iz(t).$$

Further data can be found in the above-mentioned prior art.

Good results are achieved with this method, if ECG signals measured under the same conditions, which also prevailed during the above-mentioned training measurements, are corrected. If these conditions change, for example if the patient changes position due to the respiration of said patient thereby causing the position of the ECG measuring device in the magnetic resonance device to change as well, the result of the interference estimate deteriorates, so that residual interference cannot be avoided and an ECG signal cannot be corrected optimally.

SUMMARY OF THE INVENTION

The object of the invention is therefore to specify a correction method and a magnetic resonance device, which allows reliable and fast correction of ECG signal data records measured in the magnetic resonance device even if the measuring conditions change.

According to the invention the object is achieved by a correction method and a magnetic resonance device as claimed in the claims.

An inventive correction method for correcting interference due to gradient injections in ECG signal data records, which were recorded in a magnetic resonance device by means of an ECG measuring device, hereby comprises the following steps:

- Determining a first correction data record, the ECG measuring device being in a first position,
- Determining a second correction data record, the ECG measuring device being in a second position,
- Measuring an ECG signal data record to be corrected, the ECG measuring device being in a defined position R(t),
- Defining a modified correction data record as a function of the first correction data record and the second correction data record and the first and second position and the defined position R(t) of the ECG measuring device,
- Correcting the ECG signal data record to be corrected with the aid of the modified correction data record.

With the inventive correction method it is now possible to use two correction data records, one determined in a first position and one in a second position to calculate a further correction data record, which applies in a further defined position. The quality of correction of the ECG data records is thus significantly improved compared with the above-mentioned prior art. It is thus also possible to trigger the magnetic resonance device more precisely and reliably at R-waves of an ECG signal, resulting in better image quality.

An inventive magnetic resonance device comprises an ECG measuring device, a movement capturing unit to capture a position of the ECG measuring device as a function of time and a correction data record determination unit to determine first and second correction data records, which work together in such a manner that the magnetic resonance device can be used to carry out an inventive correction method.

The method-related advantages apply in a similar manner to an inventive magnetic resonance device.

BRIEF DESCRIPTION OF THE DRAWINGS

Further advantages and details of the present invention will emerge from the exemplary embodiments described below and with reference to the drawings. The examples cited do not represent any restriction of the invention. In the drawings.

DETAILED DESCRIPTION OF THE INVENTION

Figure 1:
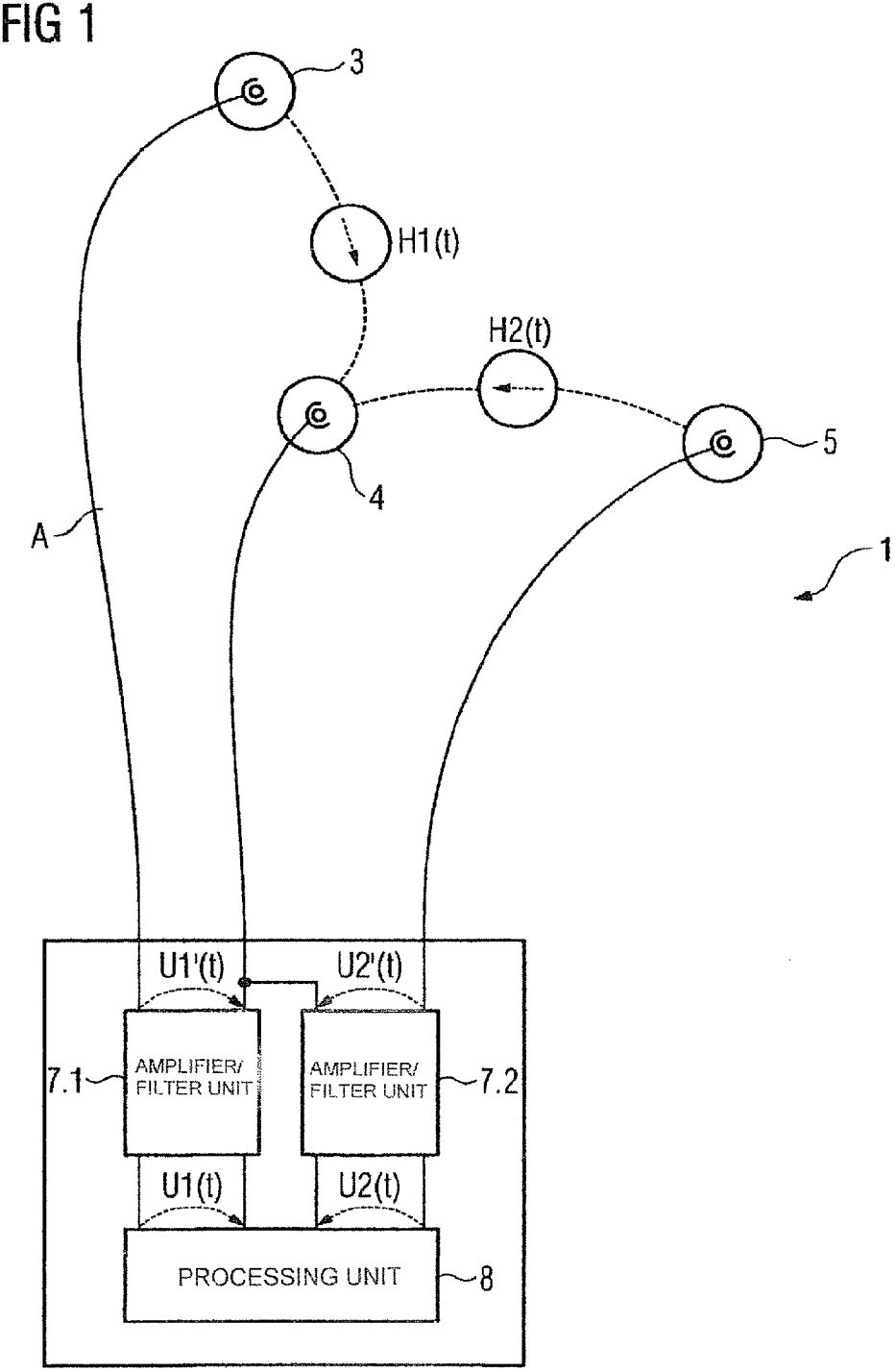
FIG. 1 shows a schematic diagram of a conventional ECG measuring device to illustrate the problems.

To illustrate the main problems underlying the invention and to introduce the variables used below, FIG. 1 shows a schematic diagram of a conventional ECG measuring device 1. This comprises three electrodes 3,4,5, which are attached to a patient (not shown) in the usual manner. Each set of two electrodes, in this instance 3 and 4 or 4 and 5, is connected by way of cables to an amplifier/filter unit 7.1 or 7.2. The amplifier/filter units 7.1 and 7.2 each measure the voltages U1'(t) and U2'(t) present between the incoming cables and forward them as ECG signals U1(t) and U2(t) to a further processing unit 8, in which the signals can for example be converted to digital signals, stored and/or otherwise processed.

The amplifier/filter units 7.1 and 7.2 can be described according to systems theory by their pulse responses h U1' U1(t) and/or h U2' U2(t) and the following applies:

$$U1(t)=U1'(t)*h\ U1'U1(t) \text{ and/or}$$

$$U2(t)=U2'(t)*h\ U2'U2(t)$$

Between the electrodes 3 and 4 is a voltage H1(t) generated by the dipole field of the heart. Similarly a voltage H2(t) is present between the electrodes 4 and 5.

Ideally H1(t)=U1'(t) and H2(t)=U2'(t). However, as described above, magnetic fields, which change over time, such as gradient fields in particular for local coding of magnetic resonance recordings, are injected as interference voltages into the current paths formed by the electrodes and their cables, so that for the signals Uj(t) (j=1,2) measured at the channels j of the ECG measuring device 1, the following applies:

$$\begin{aligned}Uj(t) &= UjECG(t) + Sj(t) \\ &= Hj(t)*hUj'Uj(t) + hIxUj(t)*Ix(t) + hIyUj(t)*Iy(t) + \\ &\quad hIzUj(t)*Iz(t)\end{aligned}$$

Although the method is always described below with reference to the example of an ECG measuring device 1 with three electrodes 3,4,5 and two ECG channels j=1,2 as shown in FIG. 1, it is not restricted to this example but can be extended in a similar manner to ECG measuring devices with more than three electrodes and/or more than two channels j=1 . . . N.

As similarly already described above, a method is known in the prior art, which estimates the interference voltages Sj(t) in defined conditions. To this end the pulse responses h Ii Uj est(t) (i=x,y,z; j=1,2) must be estimated with the aid of training measurements. The estimated interference voltages Sj est(t) thus obtained form correction data records, which can be used to correct the ECG signals Uj(t), by subtracting the estimated interference voltages Sj est(t) from the measured ECG signals Uj(t). This functions well, as long as conditions, in particular the position of the ECG measuring device, in the magnetic resonance device are the same when recording the ECG signals Uj(t) as during the training measurements.

If the ECG measuring device is moved in the meantime, for example by the respiration of a patient to be examined on a couch of the magnetic resonance device, it is no longer possible to correct ECG data records measured under changed conditions, such as a changed position, in a reliable manner with the aid of the pulse responses estimated by means of the training measurement.

To understand how this problem is to be resolved, let us look first by way of example at a pulse response h Ix U1(t).

This can be modeled based on systems theory, being split into a first subsystem and a second subsystem in the process. The first subsystem describes how the current Ix(t) is transformed by the x-axis gradient coil into a magnetic field B, the change in which causes a voltage U1 ind(t) to be induced in the current path of the electrodes 3 and 4, which is superimposed at the input of the amplifier/filter unit 7.1 on the voltage H1(t) generated by the dipole field of the heart. The second subsystem models the pulse response of the amplifier/filter unit 7.1. The following therefore applies:

$$h\ Ix\ U1(t) = h\ Ix\ U1'(t) * h\ U1'U1(t).$$

In this process the second subsystem is the pulse response h Ix U1($t$), i.e. h U1' U1($t$), irrespective of the patient and the ECG measuring device and its position in the magnetic resonance device. It is sufficient therefore henceforth just to consider the pulse response of the first subsystem h Ix U1'($t$).

The current Ix(t) enters a magnetic field Bx(x,y,z,Ix(t)) generated by the current Ix(t) by means of the x-axis gradient coil in a linear manner (the same applies for By and Bz). The voltage U1'($t$) at the input of the amplifier/filter unit 7.1 is made up, as described above, of the voltage H1($t$) generated by the dipole field of the heart and the voltage U1 ind(t) induced by the respective current flow into the x, y and z-axis gradient coils:

$$U1'(t) = H1(t) + U1ind(t)$$

$$= H1(t) - \left( \oiint_A Bx(x, y, z, Ix(t)) \cdot da + \oiint_A By(x, y, z, Iy(t)) \cdot da + \oiint_A Bz(x, y, z, Iz(t)) \cdot da \right)$$

Here A represents the surface bordered by the current path of the electrodes 3 and 4, in other words by the cables of the electrodes 3 and 4 and the voltage taps H1($t$) and U1'($t$). Since the currents enter the B fields in a linear manner and are independent of the location coordinates x,y,z, the following can be written:

$$U1'(t) = H1(t) + Ix(t) \cdot \underbrace{\oiint_A fx(x, y, z) \cdot da}_{Kx} + Iy(t) \cdot \underbrace{\oiint_A fy(x, y, z) \cdot da}_{Ky} + Iz(t) \cdot \underbrace{\oiint_A fz(x, y, z) \cdot da}_{Kz}$$

Here fx(x,y,z), fy(x,y,z) and fz(x,y,z) are vector-valued functions, which indicate the field profile of the x, y, and z-axis gradient coils at any coordinates, their amplitude at any coordinate being proportional to the respective magnetic field strength.

According to the above considerations the pulse responses h Ix U1($t$), h Iy U1($t$), h Iz U1($t$) are proportional to the coupling factors Kx, Ky, Kz. The above integrals are therefore only a function of the form of the surface A and its position in the magnetic field.

The reasons for the uncertainty of the estimate of pulse responses subject to movement influences, such as respiratory influences, is therefore precisely this dependency of the factors Kx, Ky, Kz on the position of the surface A in the magnetic field.

A relatively large change due to respiratory movement can be anticipated for the factor Ky in particular, as the surface A is located on the ribcage and is moved predominantly in the y-direction as a result of inward and outward respiration.

According to the invention provision is therefore made to define a further modified correction data record 16 by means of a first correction data record 14.1 defined in a first position of the ECG measuring device and a second correction data record 14.2 defined in a second position of the ECG measuring device, this further modified correction data record 16 being applicable for a further position of the ECG measuring device. In this process the first correction data record 14.1 is based on the pulse responses h1 Ii Uj est(t) estimated in the first position and the second correction data record 14.2 is based on the pulse responses h2 Ii Uj est(t) estimated in the second position (i=x,y,z; j=1,2).

A maximum value and/or minimum value of the movement is/are advantageously selected as the first and/or second position. In other words for a respiratory movement the first position is for example the position assumed by the ECG measuring device when a patient to be examined holds his/her breath after breathing in. In this example the second position would then correspondingly be the position assumed by the ECG measuring device when a patient to be examined holds his/her breath after breathing out. The extreme values of the pulse responses h Ix Uj(t), h Iy Uj(t), h Iz Uj(t) are thus known from the estimated values h1 Ii Uj est(t)=h Ii Uj est in(t) and h2 Ii Uj est(t)=h Ii Uj est out(t) (i=x,y,z; j=1,2).

A further set of pulse responses can now be calculated as a function of these pulse responses for example by interpolation, it being possible for this further set to be used to define a modified correction data record, which applies in a further position. To define the first, second and further position a known movement capturing unit is advantageously used, for example of the magnetic resonance device, which shows the position of the ECG measuring device as a function of time.

In the case of a respiratory movement the periodic respiratory signal R(t) for example can be defined by means of a respiratory belt or the like. In a simple exemplary embodiment the further pulse responses h' Ii Uj est(t) are defined for the modified correction data record using the movement signal, in this instance the respiratory movement R(t) and the estimated pulse responses h1 Ii Uj est(t)=h Ii Uj est in(t) and h2 Ii Uj est(t)=h Ii Uj est out(t), between which is interpolated:

h'Ii Uj est(t)=[h Ii Uj est in(t)–h Ii Uj est out(t)]/(Rin–Rout)

*(R(t)–Rout)+h Ii Uj est out(t).

Here R in indicates the value of the respiration signal in the first position and R out the value of the respiration signal in the second position.

In the example given a linear interpolation is therefore carried out between the pulse responses h1 Ii Uj est(t) and h2 Ii Uj est(t) estimated in the first and second position, based on a determined movement R(t). To this end the difference is formed between the pulse responses h1 Ii Uj est(t) and h2 Ii Uj est(t) and multiplied by the quotient of the difference between the further position R(t) and the second position R out as dividend and the difference between the first position R in and the second position R out as divisor and added to the pulse response h2 Ii Uj est(t) estimated in the second position.

It is now possible to use the further pulse responses h' Ii Uj est(t) as described above by forming the sum over i of the convolutions of the respective pulse responses h' Ii Uj est(t) with the corresponding current Ii(t) to calculate a further set of interference voltages S'j est(t), which forms the modified correction data record 16 and can be used to correct an ECG signal data record, which was measured in position R(t), by subtraction with a high level of precision. An ECG signal data record for example comprises ECG signals of different channels of an ECG measuring device.

Figure 2:
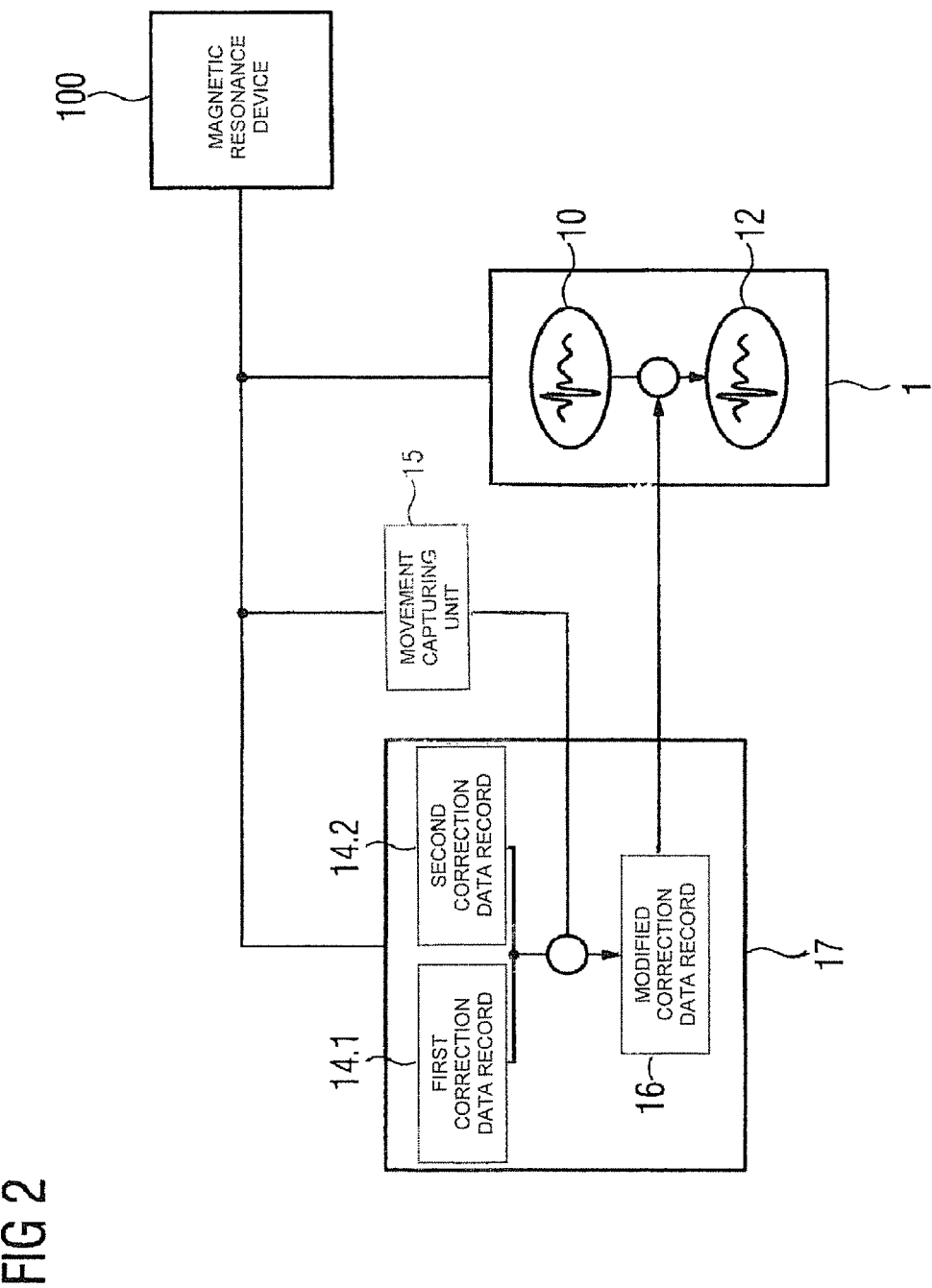
FIG. 2 shows a schematic diagram of a sequence of an inventive correction method in conjunction with an inventive magnetic resonance device.

FIG. 2 shows a schematic diagram of a sequence of the inventive correction method in conjunction with an inventive magnetic resonance device.

During an examination a patient is placed, with an ECG measuring device 1 attached, in the magnetic resonance device 100. The magnetic resonance device 100 is only shown schematically as a block here, as the basic structure of magnet unit, high-frequency coils, gradient coil unit, couch, control units, in particular also for controlling the couch, etc., is known.

According to the invention the magnetic resonance device 100 comprises in particular an ECG measuring device 1, a movement capturing unit 15 and a correction data record determination unit 17. The separate representation of these units is not necessarily physical but should instead be seen as a separation based on notional units.

The ECG measuring device 1, the movement capturing unit 15 and the correction data record determination unit 17 are connected to the magnetic resonance device 100 and one another for the transmission of data.

The ECG measuring device 1 can be used to measure and further process ECG signals 10 from a patient. This has already been described in more detail above with reference to FIG. 1. The movement capturing unit 15 is used in particular to determine a position of the ECG measuring device 1 or its movement in the magnetic resonance device 100. To this end the movement capturing unit 15 can for example capture a respiratory signal from a patient by means of a respiratory belt or the like.

The correction data record determination unit 17 allows determination of a first correction data record 14.1 and a second correction data record 14.2 according to the prior art described above, it being possible for a preparatory measurement taken in each instance before an examination, e.g. to adjust the magnetic resonance device, and acting on the ECG measuring system in the first or second position, advantageously to be used as the training measurement. The correction data record determination unit 17 is also connected to the movement capturing unit 15 in order to be able to obtain data relating to positions of the ECG measuring device 1, in particular during the determination of the correction data records 14.1 and 14.2 and during the measurement of an ECG data record 10 to be corrected. It is sufficient here to be able to define said positions in relation to one another.

According to the method described above, the correction data record determination unit 17 can define a modified correction data record 16 by interpolation from the position data and the first correction data record 14.1 and the second correction data record 14.2.

The modified correction data record 16 can be transmitted by way of a further connection to the ECG measuring device 1 and be used there to correct an ECG signal 10, which has been subject to interference due to gradient fields that are changing over time, giving a corrected ECG signal 12, in which the interference injections are largely eliminated.

The corrected ECG signal 12 can now be used for the reliable triggering of recordings of the magnetic resonance device 10.

The invention claimed is:

1. A correction method for correcting an interference due to a gradient injection in an ECG signal data record recorded in a magnetic resonance device by an ECG measuring device, comprising:
   capturing movement of the ECG measuring device as a function of time with a movement capturing unit;
   determining a first correction data record when the ECG measuring device is in a first position;
   determining a second correction data record when the ECG measuring device is in a second position wherein the first and second correction data records are determined based on a known parameter of the gradient injection comprising a current applied to a gradient coil of the magnetic resonance device;
   measuring the ECG signal data record with the ECG measuring device when the ECG measuring device is in a defined position;
   generating a modified correction data record as a function of the first correction data record and the second correction data record and the first position, the second position and the defined position of the ECG measuring device wherein the first, second and modified correction data records are determined based on estimated pulse responses;
   correcting the ECG signal data record based on the modified correction data record and;
   wherein the steps of capturing movement of the ECG measuring device, determining a first correction data record, determining a second correction data record, measuring the ECG signal data record, generating a modified correction data record and correcting the ECG signal data record are implemented in a machine that includes storage and a processing unit.

2. The correction method as claimed in claim 1, wherein the first position corresponds to a first respiratory position of a patient and the second position corresponds to a second respiratory position of the patient.

3. The correction method as claimed in claim 2, wherein the movement of the ECG measuring device is due to a respiratory movement of a patient to be examined.

4. The correction method as claimed in claim 1, wherein the first correction data record is based on a first estimated pulse response estimated in the first position and the second correction data record is based on a second estimated pulse response estimated in the second position.

5. The correction method as claimed in claim 4, wherein the modified correction data record is based on a third estimated pulse response that is interpolated between the first estimated pulse response and the second estimated pulse response.

6. The correction method as claimed in claim 5, wherein the interpolation is a linear interpolation.

7. The correction method as claimed in claim 1, wherein the modified correction data record indicates the interference and is subtracted from the ECG signal data record for correcting the interference.

8. The correction method as claimed in claim 1, wherein the first correction data record and the second correction data record are determined by a training measurement.

9. The correction method as claimed in claim 8, wherein the training measurement is a preparatory measurement taken before an examination for adjusting the magnetic resonance device.

10. The correction method as claimed in claim 1, wherein the ECG measuring device comprises at least two ECG channels.

11. A magnetic resonance device, comprising:
    a magnetic resonance imaging device including a magnet unit, high-frequency coils, gradient coil unit, patient couch and control unit;
    an ECG measuring device that records an ECG signal data record in a defined position;
    a movement capturing unit that captures a movement of the ECG measuring device as a function of time; and
    a correction data record determination unit for:
       determining a first correction data record when the ECG measuring device is in a first position, determining a second correction data record when the ECG measuring device is in a second position wherein a gradient injection in the ECG signal data record causes an interference in the ECG signal data record and the first and second correction data records are determined based on a known parameter of the gradient injection comprising a current applied to a gradient coil of the magnetic resonance device, generating a modified correction data record as a function of the first correction data record and the second correction data record and the first position the second position and the defined position of the ECG measuring device wherein the first, second and modified correction data records are determined based on estimated pulse responses, and correcting the ECG signal data record based on the modified correction data record.

12. The magnetic resonance device as claimed in claim 11, wherein the movement capturing unit is a respiratory movement capturing unit.

13. The magnetic resonance device as claimed in claim 12, wherein the respiratory movement capturing unit is a respiratory belt.

* * * * *